(12) United States Patent
Korkuch et al.

(10) Patent No.: US 11,944,770 B2
(45) Date of Patent: Apr. 2, 2024

(54) EXPANDABLE SHEATH WITH INTERLOCK DILATOR

(71) Applicant: ABIOMED, Inc., Danvers, MA (US)

(72) Inventors: Christopher N. Korkuch, Danvers, MA (US); Robert Fishman, Danvers, MA (US); Michael Thomas Finnegan, Danvers, MA (US); Charles DeLorenzo, Danvers, MA (US); Andrew Gentile, Danvers, MA (US); Anne Gabrielle McLoughlin, Danvers, MA (US); Robert Swierczek, Danvers, MA (US); Matthew D'Agostino, Danvers, MA (US); Jonathan Barry, Danvers, MA (US)

(73) Assignee: Abiomed, Inc., Danvers, MA (US)

(*) Notice: Subject to any disclaimer, the term of this patent is extended or adjusted under 35 U.S.C. 154(b) by 0 days.

(21) Appl. No.: 18/131,608

(22) Filed: Apr. 6, 2023

(65) Prior Publication Data

US 2023/0347121 A1    Nov. 2, 2023

Related U.S. Application Data

(63) Continuation of application No. 17/165,421, filed on Feb. 2, 2021, now Pat. No. 11,660,434.

(Continued)

(51) Int. Cl.
  *A61M 29/02*    (2006.01)
  *A61B 17/34*    (2006.01)
  *A61M 60/165*    (2021.01)

(52) U.S. Cl.
  CPC ......... *A61M 29/02* (2013.01); *A61B 17/3468* (2013.01); *A61M 2029/025* (2013.01);

(Continued)

(58) Field of Classification Search
  CPC .... A61M 2029/1077; A61M 2029/025; A61M 2205/0266; A61M 2205/0238; A61M 60/165; A61M 29/02; A61B 17/3468
  See application file for complete search history.

(56) References Cited

U.S. PATENT DOCUMENTS

| | | | |
|---|---|---|---|
| 4,699,611 | A | 10/1987 | Bowden |
| 5,139,486 | A | 8/1992 | Moss |

(Continued)

FOREIGN PATENT DOCUMENTS

| | | | |
|---|---|---|---|
| EP | 0383426 | A1 | 8/1990 |
| EP | 0792660 | A2 | 9/1997 |

(Continued)

OTHER PUBLICATIONS

International Preliminary Report on Patentability and Written Opinion for International Application No. PCT/US2018/021695 dated Sep. 10, 2019 (6 pages).

(Continued)

*Primary Examiner* — Jocelin C Tanner
(74) *Attorney, Agent, or Firm* — Botos Churchill IP Law LLP

(57) ABSTRACT

An expandable introducer sheath with an interlock dilator. The present technology provides an expandable sheath with a step feature inside its distal opening, and a dilator with an interlock that includes a catch surface configured to engage with the step feature and resist further relative movement so that the body of the dilator is prevented from exiting the distal end of the expandable sheath. This interlocking engagement may allow the dilator to be used to extend and maintain tension on the expandable sheath during insertion into a patient, and then to be retracted from the expandable sheath by pulling the dilator in the opposite direction. The present technology also provides a dilator hub with a spring mechanism configured to achieve and maintain a desired (Continued)

tension on the expandable sheath and to prevent overextension of the expandable sheath when the dilator is being inserted into the expandable sheath.

33 Claims, 11 Drawing Sheets

Related U.S. Application Data

(60) Provisional application No. 62/969,318, filed on Feb. 3, 2020.

(52) U.S. Cl.
CPC ... *A61M 60/165* (2021.01); *A61M 2205/0238* (2013.01); *A61M 2205/0266* (2013.01)

(56) References Cited

U.S. PATENT DOCUMENTS

| | | |
|---|---|---|
| 5,234,425 A | 8/1993 | Fogarty et al. |
| 5,304,142 A | 4/1994 | Liebl et al. |
| 5,320,611 A | 6/1994 | Bonutti et al. |
| 5,395,341 A | 3/1995 | Slater |
| 5,397,310 A | 3/1995 | Chu et al. |
| 5,407,430 A | 4/1995 | Peters |
| 5,488,960 A | 2/1996 | Toner |
| 5,492,530 A | 2/1996 | Fischell et al. |
| 5,536,255 A | 7/1996 | Moss |
| 5,573,517 A | 11/1996 | Bonutti et al. |
| 5,653,697 A | 8/1997 | Quiachon et al. |
| 5,814,058 A | 9/1998 | Carlson et al. |
| 5,911,702 A | 6/1999 | Romley et al. |
| 5,935,122 A | 8/1999 | Fourkas et al. |
| 5,944,691 A | 8/1999 | Querns et al. |
| 5,971,993 A | 10/1999 | Hussein et al. |
| 6,120,480 A | 9/2000 | Zhang et al. |
| 6,197,016 B1 | 3/2001 | Fourkas et al. |
| 6,338,730 B1 | 1/2002 | Bonutti et al. |
| 6,428,556 B1 | 8/2002 | Chin |
| 6,458,867 B1 | 10/2002 | Wang et al. |
| 6,579,264 B1 | 6/2003 | Rossi |
| 6,613,038 B2 | 9/2003 | Bonutti et al. |
| 6,692,462 B2 | 2/2004 | MacKenzie et al. |
| 6,814,715 B2 | 11/2004 | Bonutti et al. |
| 6,989,003 B2* | 1/2006 | Wing .............. A61B 17/34 604/161 |
| 7,025,746 B2 | 4/2006 | Tal |
| 7,722,567 B2 | 5/2010 | Tal |
| 7,727,251 B2 | 6/2010 | Spurchise et al. |
| 7,927,309 B2 | 4/2011 | Palm |
| 8,475,431 B2 | 7/2013 | Howat |
| 8,597,277 B2 | 12/2013 | Lenker et al. |
| 8,663,541 B2 | 3/2014 | Chun et al. |
| 8,672,888 B2 | 3/2014 | Tal |
| 8,758,402 B2 | 6/2014 | Jenson et al. |
| 8,814,832 B1 | 8/2014 | Al-Rashdan et al. |
| 9,126,015 B2 | 9/2015 | Krolik et al. |
| 9,320,508 B2 | 4/2016 | Carroux |
| 9,446,218 B2 | 9/2016 | Accisano |
| 9,474,884 B1 | 10/2016 | Aman et al. |
| 9,586,033 B2 | 3/2017 | Tegels |
| 9,693,800 B2 | 7/2017 | Aman et al. |
| 9,895,245 B2 | 2/2018 | Puckett et al. |
| 9,974,561 B2 | 5/2018 | Benning et al. |
| 10,143,491 B2 | 12/2018 | Clancy et al. |
| 10,449,071 B2 | 10/2019 | Jordan |
| 10,499,895 B2 | 12/2019 | Anderson |
| 10,537,718 B2 | 1/2020 | Lederman et al. |
| 10,625,050 B2 | 4/2020 | McFarland |
| 10,682,157 B2 | 6/2020 | Bierman et al. |
| 10,695,531 B2 | 6/2020 | Suzuki |
| 10,874,511 B2 | 12/2020 | Ginn |
| 2002/0072712 A1 | 6/2002 | Nool et al. |
| 2003/0014068 A1 | 1/2003 | Bonutti et al. |
| 2004/0044330 A1* | 3/2004 | Li .............. A61J 15/0026 604/535 |
| 2005/0149105 A1 | 7/2005 | Leeflang et al. |
| 2006/0041270 A1 | 2/2006 | Lenker et al. |
| 2006/0135981 A1 | 6/2006 | Lenker et al. |
| 2006/0287574 A1 | 12/2006 | Chin |
| 2006/0287669 A1 | 12/2006 | Casey et al. |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0082165 A1 | 4/2008 | Wilson et al. |
| 2008/0183136 A1 | 7/2008 | Lenker et al. |
| 2009/0240202 A1 | 9/2009 | Drasler et al. |
| 2009/0259200 A1 | 10/2009 | Lampropoulos et al. |
| 2010/0198160 A1 | 8/2010 | Voss |
| 2011/0144690 A1 | 6/2011 | Bishop et al. |
| 2011/0152763 A1 | 6/2011 | Bishop et al. |
| 2011/0166637 A1 | 7/2011 | Irwin et al. |
| 2012/0035548 A1 | 2/2012 | MacKenzie et al. |
| 2012/0109056 A1 | 5/2012 | Rasmussen |
| 2012/0130192 A1 | 5/2012 | Rasmussen et al. |
| 2013/0131718 A1 | 5/2013 | Jenson et al. |
| 2013/0131787 A1 | 5/2013 | Ginn |
| 2013/0138201 A1 | 5/2013 | Ginn |
| 2013/0184736 A1* | 7/2013 | Aman .............. A61M 25/0074 606/191 |
| 2013/0317438 A1 | 11/2013 | Ellingwood et al. |
| 2013/0317481 A1 | 11/2013 | Ellingwood et al. |
| 2013/0338677 A1 | 12/2013 | Schwitzer et al. |
| 2014/0275795 A1 | 9/2014 | Little et al. |
| 2014/0336752 A1 | 11/2014 | Ginn et al. |
| 2015/0094795 A1 | 4/2015 | Ginn et al. |
| 2016/0066948 A1 | 3/2016 | Ellingwood et al. |
| 2016/0067454 A1 | 3/2016 | Furnish et al. |
| 2016/0128723 A1 | 5/2016 | Ginn et al. |
| 2016/0220358 A1 | 8/2016 | Wilson et al. |
| 2016/0296737 A9 | 10/2016 | Aman et al. |
| 2016/0338828 A1 | 11/2016 | Ginn |
| 2016/0354583 A1 | 12/2016 | Ellingwood et al. |
| 2017/0000973 A1 | 1/2017 | Otake et al. |
| 2017/0014232 A1 | 1/2017 | Ginn et al. |
| 2017/0056063 A1 | 3/2017 | Ellingwood et al. |
| 2017/0080180 A1 | 3/2017 | Eilat |
| 2017/0095640 A1 | 4/2017 | Rogers et al. |
| 2017/0265891 A1 | 9/2017 | McFarland |
| 2017/0281908 A1 | 10/2017 | Ellingwood et al. |
| 2018/0071091 A9 | 3/2018 | Ginn et al. |
| 2018/0256859 A1 | 9/2018 | Korkuch |
| 2018/0271558 A1 | 9/2018 | Bierman et al. |
| 2018/0325706 A1 | 11/2018 | Hebert et al. |
| 2019/0030294 A1 | 1/2019 | McLaughlin et al. |
| 2019/0070394 A1 | 3/2019 | Appling et al. |
| 2019/0183525 A9 | 6/2019 | Ginn et al. |
| 2019/0247617 A1 | 8/2019 | Farnan |
| 2019/0247627 A1 | 8/2019 | Korkuch et al. |
| 2019/0307589 A1 | 10/2019 | Goldberg et al. |
| 2020/0360140 A1 | 11/2020 | Ginn et al. |
| 2020/0360165 A1 | 11/2020 | Ginn et al. |
| 2020/0367929 A1 | 11/2020 | Ginn et al. |

FOREIGN PATENT DOCUMENTS

| | | |
|---|---|---|
| EP | 2179762 A1 | 4/2010 |
| EP | 2676641 A2 | 12/2013 |
| EP | 2995268 A1 | 3/2016 |
| JP | 2008011867 A | 1/2008 |
| JP | 5199434 B2 | 2/2013 |
| JP | 2016189839 A | 11/2016 |
| JP | 2019076330 A | 5/2019 |
| WO | 2004037333 A1 | 5/2004 |
| WO | 2019008922 A1 | 1/2019 |

OTHER PUBLICATIONS

International Preliminary Report on Patentability and Written Opinion for International Application No. PCT/US2019/018275 dated Aug. 27, 2020 (14 pages).

(56) References Cited

OTHER PUBLICATIONS

International Search Report and Written Opinion for International Application No. PCT/US2018/021695 dated Jun. 22, 2018 (9 pages).
International Search Report and Written Opinion for International Application No. PCT/US2019/018275 dated Jul. 15, 2019 (23 pages).
International Search Report and Written Opinion for International Application No. PCT/US2019/046543 dated Jan. 10, 2020 (23 pages).
International Search Report and Written Opinion for International Application No. PCT/US2021/070113 dated Aug. 10, 2021 (4 pages).

* cited by examiner

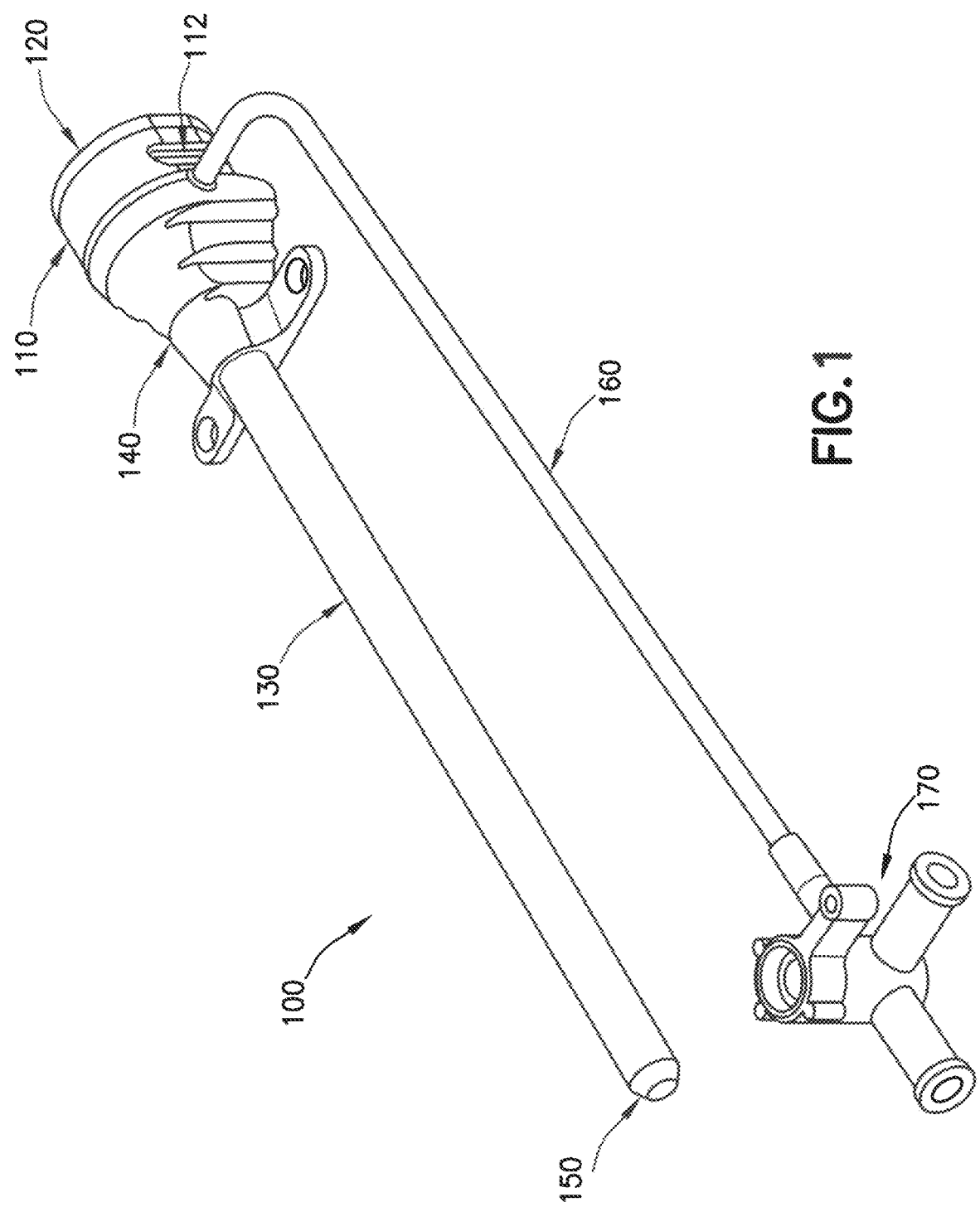

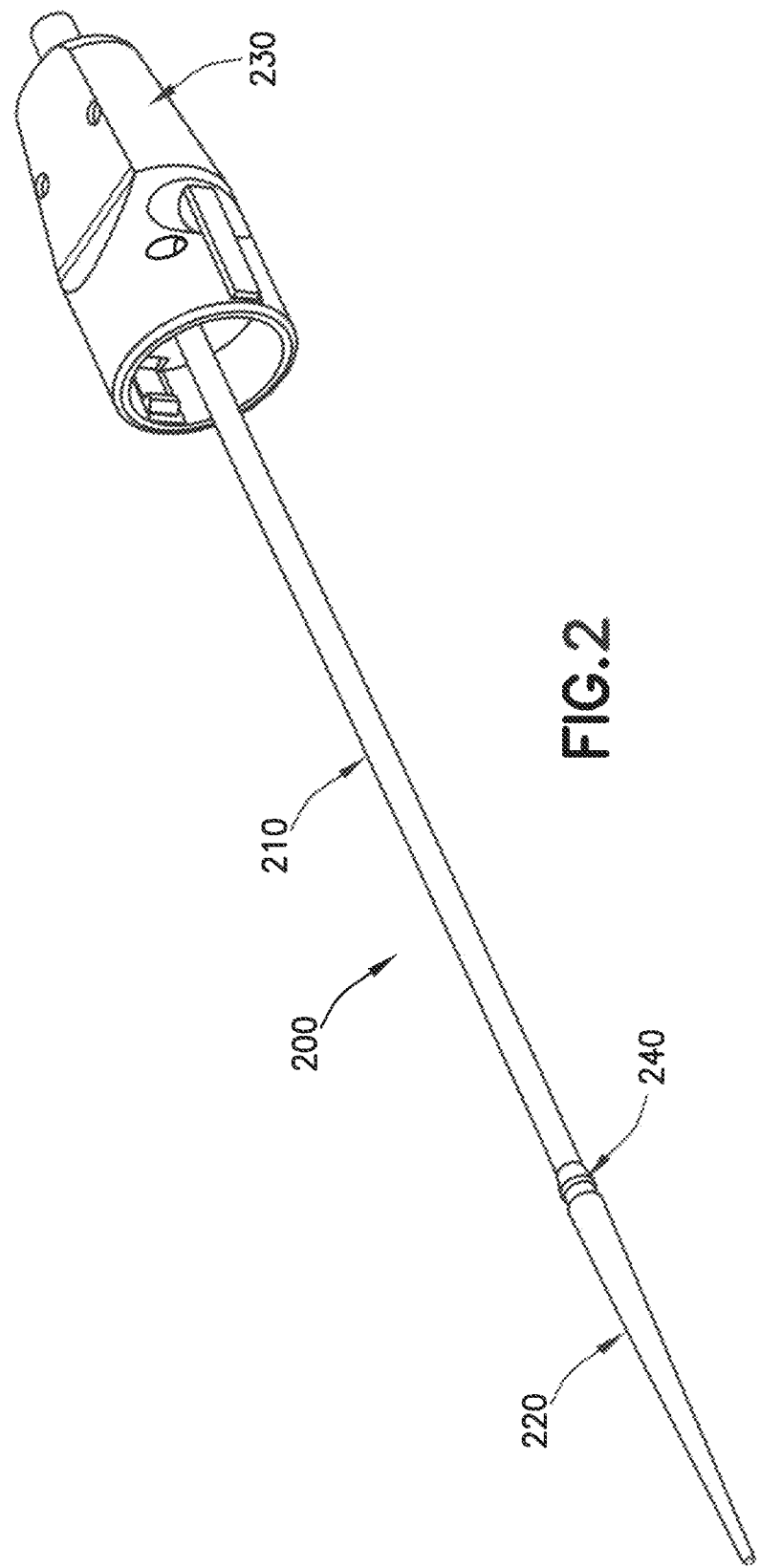

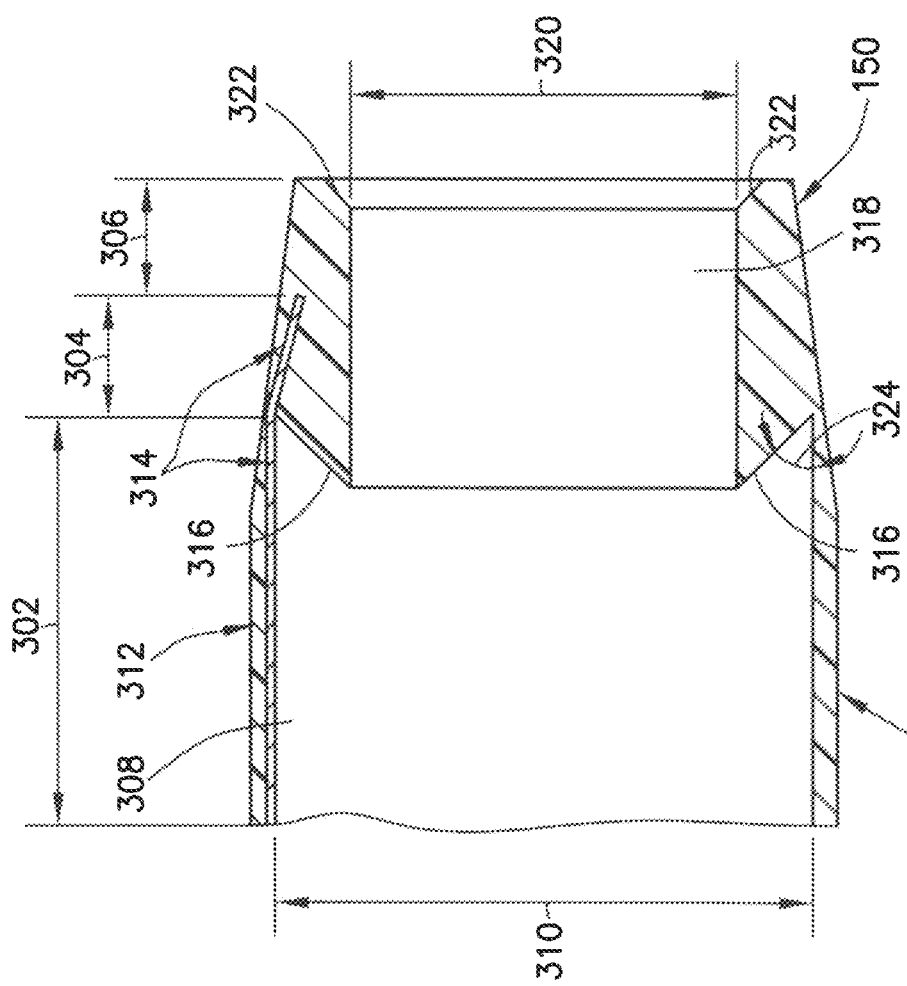

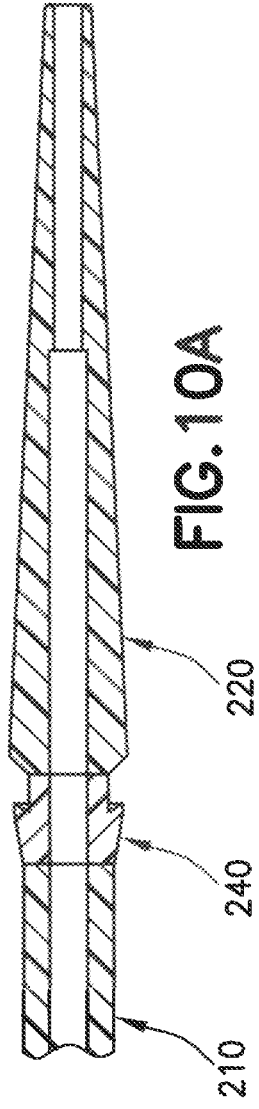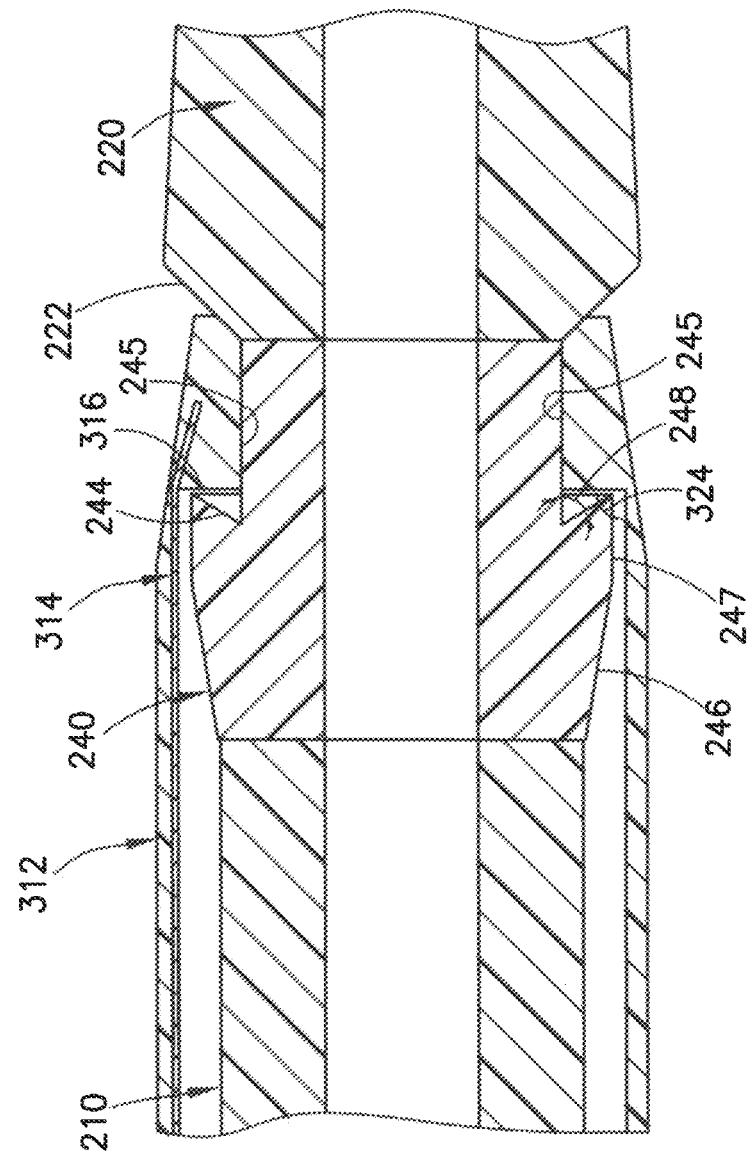

EXPANDABLE SHEATH WITH INTERLOCK DILATOR

CROSS-REFERENCE TO RELATED APPLICATIONS

The present application is a continuation of U.S. application Ser. No. 17/165,421, filed Feb. 2, 2021, now issued U.S. Pat. No. 11,660,434, which claims priority to U.S. Provisional Application No. 62/969,318, filed Feb. 3, 2020, the entire disclosures of which are incorporated by reference herein. This application is related to U.S. Patent Publication No. 2019/0247627A1 entitled "Expandable Introducer Sheath for Medical Device" which was filed as U.S. application Ser. No. 16/277,378 on Feb. 15, 2019, which is incorporated by reference herein. This application is also related to U.S. Patent Publication No. 2018/0256859A1 entitled "Expandable Introducer Sheath for Medical Device," which was filed as U.S. application Ser. No. 15/917,042 on Mar. 9, 2018, which is incorporated by reference herein.

BACKGROUND

Intracardiac heart pump assemblies can be introduced into the heart either surgically or percutaneously and used to deliver blood from one location in the heart or circulatory system to another location in the heart or circulatory system. For example, when deployed in the heart, an intracardiac pump can pump blood from the left ventricle of the heart into the aorta, or pump blood from the inferior vena cava into the pulmonary artery. Intracardiac pumps can be powered by a motor located outside of the patient's body (and accompanying drive cable) or by an onboard motor located inside the patient's body. Some intracardiac blood pump systems can operate in parallel with the native heart to supplement cardiac output and partially or fully unload components of the heart. Examples of such systems include the IMPPELLA® family of devices (Abiomed, Inc., Danvers Mass.).

In one common approach, an intracardiac blood pump is inserted by a catheterization procedure through the femoral artery using a sheath, such as a peel away introducer sheath. The sheath can alternatively be inserted in other locations such as in the femoral vein or any path for delivery of a pump for supporting either the left or right side of the heart.

The introducer sheath can be inserted into the femoral artery through an arteriotomy to create an insertion path for the pump assembly. A portion of the pump assembly is then advanced through an inner lumen of the introducer and into the artery. Once the pump assembly has been inserted, the introducer sheath is peeled away. A repositioning sheath can then be advanced over the pump assembly and into the arteriotomy. Replacing the introducer sheath with the repositioning sheath during insertion of a medical device can reduce limb ischemia and bleeding at the insertion site in the skin (and/or at the insertion site within the vessel) because of better fixation of the sheath to the patient when used with a hemostatic valve.

Since commercially available tear away introducer sheaths are not radially expandable, the inner diameter of the introducer sheath must always be large enough to accommodate the largest diameter portion of the pump assembly such as the pump head even if other parts of the pump assembly, such as the catheter, have a significantly smaller diameter. In this example, the introducer creates an opening that has an outer diameter wider than necessary to allow passage of the pump catheter into the vessel. Then, the introducer sheath is peeled or torn away and replaced with a lower-profile repositioning sheath. Removing the introducer sheath by peeling it away presents several challenges. For example, introducers can tear too easily and/or prematurely, leading to bleeding or vascular complications. Some introducers may require excessive force to tear away for removal. If a physician applies too much force, when the introducer finally tears, the physician may inadvertently shift the position of the pump within the heart. This configuration also complicates the design of the hemostatic valve located in the hub of the introducer which also needs to tear. Further, a peel away introducer sheath leads to a larger vessel opening after the system is removed, which can complicate vessel closure.

Medical introducers for other applications than inserting heart pumps have expandable sheath bodies which may expand radially to allow passage of percutaneous devices into the patient's vasculature. These existing expandable introducers are for relatively short-term use and may be designed to prevent thrombosis between the sheath body and an indwelling catheter.

These introducers are inserted having inner diameters smaller than the outer diameter of the device being introduced. The introducers expand to allow passage of the device through the sheath and into the vasculature and then may shrink again after the device has passed. In the current state of the industry, these expandable introducers require a distinct expandable feature, e.g., a longitudinal fold or crease or a lumen for injection of a fluid (e.g., saline) to transition from a compressed state to an expanded state. Because these existing expandable introducers are intended for relatively short-term use, clot formation on the outside of the introducer sheath may be unlikely. However, if left in for longer periods of time (e.g., >1 hour, >2 hours, >6 hours, >1 day, >2 days, >1 week), clots may form on the outside surface of the expandable sheath mesh, and risk being dislodged into the blood stream at a later time. Additionally, some commercially available expandable sheaths are completely flexible and therefore do not provide any rigidity within their structure thereby leading to kinking or buckling during insertion or withdrawal of a percutaneous medical device.

BRIEF SUMMARY

The present technology relates to an expandable introducer sheath with an interlock dilator. More particularly, the present technology provides an expandable sheath with a step feature inside its distal opening, and a dilator with an interlock that includes a catch surface that is configured to engage with the step feature of the expandable sheath. When the step feature engages the catch surface, it resists further relative movement so that the body of the dilator is prevented from exiting the distal end of the expandable sheath. The nature of the interlocking engagement between the step feature and the catch surface allows the dilator to be used to extend and maintain tension on the expandable sheath during insertion into a patient, and then to be retracted from the expandable sheath by simply pulling the dilator in the opposite direction. The present technology also provides a dilator hub with a spring mechanism configured to achieve and maintain a desired tension on the expandable sheath and to prevent overextension of the expandable sheath when the dilator is being inserted into the expandable sheath.

One aspect of the present disclosure relates to an apparatus comprising an expandable sheath and a dilator. The expandable sheath comprises a cylindrical or substantially cylindrical expandable frame having a proximal opening, a distal opening, an inner surface, and an outer surface. The expandable sheath further comprises a material covering the outer surface of the expandable frame and a portion of the inner surface of the expandable frame, and forming a step feature within the distal opening, the step feature having a first surface that abuts the inner surface of the expandable frame and that is oriented at a first angle relative to the inner surface of the expandable frame. The dilator comprises a cylindrical or substantially cylindrical body, a tapered tip, and an interlock between the body and the tapered tip. The interlock has a first cylindrical section with a first outer diameter, a second cylindrical section with a second outer diameter that is less than the first diameter, and a catch surface that abuts the first cylindrical section and that is oriented at a second angle relative to the first cylindrical section. The dilator is configured to be inserted into the expandable sheath through the proximal opening of the expandable frame. The catch surface is configured to engage the first surface to resist the body of the dilator from passing out of the expandable frame through the distal opening.

In some aspects, the apparatus may further comprise a sheath hub configured to secure the expandable sheath proximate to the distal opening of the expandable frame, and a dilator hub. The dilator hub comprises a dilator insert mold configured to secure the body of the dilator; a spring configured to engage the dilator insert mold, and resist movement of the dilator insert mold within the dilator hub; and one or more latches configured to lock the dilator hub to the sheath hub.

In some aspects, the interlock further comprises a tapered section that abuts the second cylindrical section. In some aspects, the tapered section is further configured to engage a portion of the material proximate to the distal opening of the expandable frame.

In some aspects, the first angle is ninety degrees. In other aspects, the first angle is less than ninety degrees.

In some aspects, the second angle is ninety degrees. In other aspects, the second angle is less than ninety degrees.

In some aspects, the step feature has a radial height of between 0.1 mm and 5 mm.

In some aspects, the material is a polymer, such as thermoplastic polyurethane.

In some aspects, the expandable frame is a braided material, and may comprise strands of nitinol.

In some aspects, the expandable sheath further comprises a coating applied to the expandable frame and the material, such as a lubricious coating.

In some aspects, the interlock is formed of stainless steel, and may further be coated with a polymer. In other aspects, the interlock is formed of a polymer.

In some aspects, the tapered tip is formed of a polymer, such as polyether block amide.

BRIEF DESCRIPTION OF DRAWINGS

FIG. 1 illustrates a sheath assembly;

FIG. 2 illustrates a dilator assembly;

FIG. 9 is a cross-sectional side view of a distal end of the sheath assembly of FIG. 1 according to aspects of the disclosure.

FIG. 10A is a cross-sectional side view of a portion of a dilator according to aspects of the disclosure.

FIG. 10B is a close-up cross-sectional view of the components of FIG. 10A in engagement with the sheath tip of FIG. 8.

DETAILED DESCRIPTION

Figure 3A:
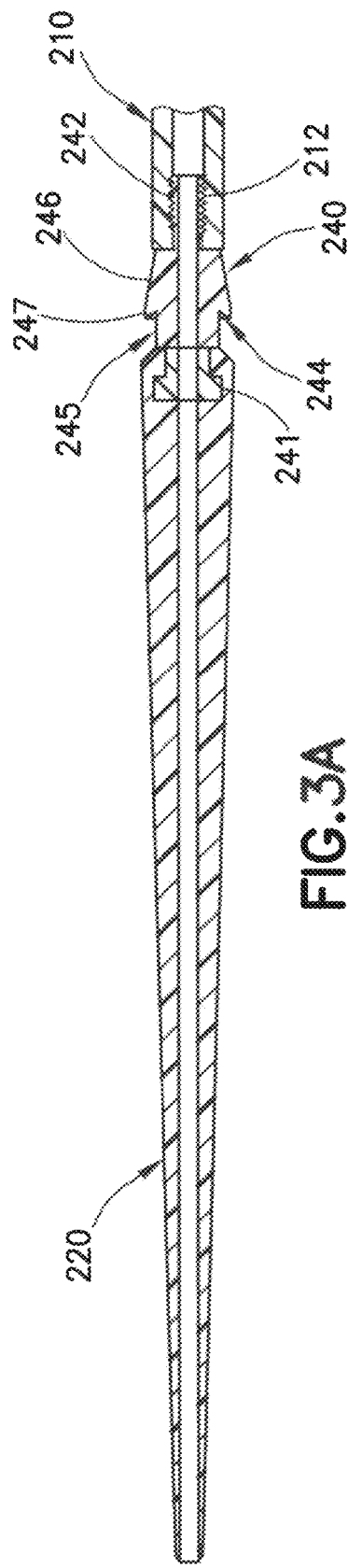
FIGS. 3A and 3B illustrate the interlock of the dilator assembly in FIG. 2.

Embodiments of the present disclosure are described in detail with reference to the figures wherein like reference numerals identify similar or identical elements. It is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

To provide an overall understanding of the systems, method, and devices described herein, certain illustrative embodiments will be described. Although the embodiments and features described herein are specifically described for use in connection with an intracardiac heart pump system, it will be understood that all the components and other features outlined below may be combined with one another in any suitable manner and may be adapted and applied to other types of medical devices such as electrophysiology study and catheter ablation devices, angioplasty and stenting devices, angiographic catheters, peripherally inserted central catheters, central venous catheters, midline catheters, peripheral catheters, inferior vena cava filters, abdominal aortic aneurysm therapy devices, thrombectomy devices, TAVR delivery systems, cardiac therapy and cardiac assist devices, including balloon pumps, cardiac assist devices implanted using a surgical incision, and any other venous or arterial based introduced catheters and devices.

The systems, methods, and devices described herein provide an expandable sheath assembly for the insertion of a medical device (e.g., an intracardiac heart pump) into a blood vessel through a vessel aperture. The expandable sheath assembly comprises a dilator assembly, and a sheath body having an inner surface and an outer surface, the inner surface defining a lumen that extends between proximal and distal ends of the sheath. Optionally, the expandable sheath assembly may include a hemostasis stylet. The expandable sheath assemblies (including the sheath body, dilator assembly, and optional hemostasis stylet) are especially advantageous over existing expandable sheath assemblies for patients with coronary artery disease (CAD) and peripheral artery disease, presenting with calcification and tortuosity of arteries, making delivery of introducer sheaths and catheters difficult. The expandable sheath assemblies herein are easier to insert than traditional assemblies because of their reduced insertion profile, increased flexibility, reduced friction, and reduced risk of kinking under loads. The reduced insertion profile minimizes insertion related complications, minimizes stretching and load on the vessel opening, and minimizes the risk of limb ischemia. The structure of the sheath body described herein provides sufficient axial stiffness for pushability and buckling resistance, while maintaining bending flexibility and kink resistance, and reduces frictional force to prevent "finger trapping." Moreover, the structures of the sheath body described herein provides an improvement over existing introducer sheath bodies by having a smooth inner surface with a thin coating thickness reducing the force required to expand the sheath (compared to the force required to expand a sheath having a coating without any bias), and/or by having a smooth outer surface reducing the risk of thrombus formation during use over longer durations while at the same time enabling the sheath to expand and contract as desired and reducing friction between the sheath body and devices being inserted through it. Furthermore, the structure of the sheath body described herein interfaces with a dilator assembly, such that the sheath body can be held in place for insertion into a body lumen by having a portion of the sheath body be constrained or entrapped in a longitudinal direction. This constraint or entrapment of the sheath body facilitates the expandable sheath body insertion in combination with a dilator assembly, without damaging the expandable sheath body or altering its properties.

The sheath body can expand between different states to accommodate the medical device. For example, the sheath body is elongated in a first smaller diameter state for insertion and relaxed into a second larger diameter state once at a desired location to allow the passage of a portion of a medical device through the lumen, the portion of the medical device having a transverse cross-sectional area larger than a transverse cross-sectional area of the lumen in the first state. In different configurations, the sheath is further expanded between a resting state when the sheath is at its desired location, and a larger diameter state when the medical device is passed through. In any configuration, the expandable sheath assemblies herein do not require additional elements relative to a standard introducer: no external balloon, no fold in the expandable sheath body, no second sheath for delivery. This can be advantageous over existing expandable sheath assemblies by simplifying the use of the expandable sheath assembly (e.g., requiring less steps, taking less time).

Moreover, the momentary expansion of the sheath body from the elongated state to the relaxed state (or from the relaxed state to the expanded state) minimizes the size of the opening, e.g., arteriotomy, required when inserting the sheath into the vasculature of the patient. Minimizing the amount of time, the sheath body is in the expanded state also minimizes damage to a vessel wall as a smaller opening would be required to accommodate the sheath body in the relaxed or collapsed state, thereby minimizing thrombotic occlusion of the vessel. A smaller opening also minimizes the time to reach hemostasis after removal of the medical device. Such an expandable sheath does away with the need for the conventional set up of having multiple sheaths, such as a peel away introducer sheath and a repositioning sheath for the introduction of a medical device (e.g., an intracardiac heart pump) into the vessel. Such an expandable sheath also allows such a conventional set-up to be used in conjunction with it, if necessary. Once the expandable sheath is positioned in an opening of a blood vessel of a patient, it maintains access to the vessel even after the medical device is removed, should such access be required for other medical procedures. This increases procedural efficiency of any medical procedure as there is no need to re-gain alternative access or re-insert a second sheath in the same access site. The effective consolidation of the introducer sheath and the repositioning sheath into a single device decreases the costs involved during a medical procedure. Further, since only a single sheath is required to gain arteriotomic access to a vessel, less bleeding would be involved during long term use of a percutaneous medical device such as a heart pump. The integration of the sheath body and dilator assembly with the hemostasis stylet allows for titrated hemostasis at the vessel opening. In some implementations, the hemostasis stylet can be a repositioning sheath, which is also used to control blood flow along the expandable sheath and minimize bleeding.

Additionally, the expandable sheath assemblies herein are advantageous over existing expandable sheath assemblies because they maintain guidewire access throughout the full procedure by always allowing the user to remove the pump with the sheath in place.

The expandable sheath can be delivered into the patient at a small profile if held in axial tension (drawn down) prior to insertion. This has the following key benefits: i) drawing down to a small insertion profile to minimize insertion related complications (i.e., bleeding, vascular injury, high insertion forces); and ii) maintaining a "soft" sheath body and momentary expansion for interaction at the arteriotomy to allow for small bore closure and minimized bleeding due to minimized vessel recoil during use.

Previous expandable sheath delivery systems require a complex mechanism to capture the tip of the sheath, lock the sheath to the sheath hub, and draw the sheath down. This requires user manipulation at least twice, and those manipulations are typically device-specific. As such delivery systems differ from "typical" introducer systems, they may require specific training to use and may lead to use errors.

A "typical" introducer system comes packaged as a separate sheath, a separate dilator, and accessories. The user generally then removes the sheath and dilator and separately pre-flushes each with saline to remove air. The user then assembles the introducer system by inserting the dilator into the proximal end of the sheath. The introducer assembly is now ready to use.

Described herein are modifications to the tip of the sheath that allow it to "lock" to a dilator via an "interlock" feature. By so locking the dilator to the sheath, the expandable sheath introducer assembly may be inserted into the patient much like a typical introducer but retains the benefits of the expandable introducer sheath described above. This interlocking expandable introducer sheath assembly is easier to manufacture than those described above, while also being easier to use because it is operated like a typical introducer sheath assembly.

FIG. 1 shows a sheath assembly 100 in accordance with aspects of the technology. The sheath assembly has a hub 110 that locks the sheath in position once inserted. The hub 110 works in concert with the cap 120 to secure the sheath body 130 in position. The hub 110 also has detents 112 (only one of which is visible) to aid in attaching hub 110 to dilator hub 230 as described further below. The butterfly/suture pad 140 is configured to aid in attaching the sheath assembly 100 to the patient (e.g., by suturing the assembly to the patient). As can be seen, the distal end of the sheath body 130 has a tapered sheath tip 150. The sheath tip 150 may have a straight linear taper, convex taper, concave taper, or a taper composed of one or more straight, convex, and/or concave sections. The sheath tip 150 may be any suitable length. In some implementations, sheath tip 150 may be between 0.1 mm and 5 mm in length. In the present description, the proximal end of the assembly is at the hub/cap end and the distal end of the assembly is at the tip end. Fluid may be introduced into the assembly via sidearm channel 160, and fluid flow into the device may be controlled by stopcock 170. A hemostatic valve (not shown) may also be included within hub 110, the hemostatic valve being configured to prevent blood from leaking outside of the patient during insertion and/or removal of an intracardiac blood pump or other components. Although any suitable hemostatic valve may be employed, examples are described and illustrated in U.S. Provisional Application No. 62/935,300, which is hereby incorporated by reference. In addition, in some implementations, the hub 110 may include a foam insert (not shown) placed proximal to the hemostatic valve that may be soaked with a lubricant such as silicone so that components will be lubricated as they are inserted through the foam and into the sheath body 130.

The expandable sheath body 130 comprises at least a frame and a coating. A coating may be applied to the outer surface of the sheath body 130 to facilitate passage inside the patient, known as an outer-diameter biased approach. In some implementations, the coating may be a polymer such as the polymer material 312 shown and described with respect to FIGS. 8-10. This outer-diameter biased coating advantageously provides a smooth outer surface which reduces the risk of clot formation and minimizes friction when inserting a device through the expandable sheath. For example, the use of a smooth outer surface advantageously minimizes the risk of clots forming on the surface of the expandable sheath body 130, and a corrugated inner surface minimizes the surface area of the expandable sheath in contact with a device being pushed through, thereby minimizing associated friction forces. In some implementations, the corrugated inner surface may be a braided material such as the braided material 314 shown and described with respect to FIGS. 8-10. In some implementations, an additional lubricious coating may be applied to the inner and/or outer surfaces of sheath body 130, i.e., covering polymer material 312 and/or braided material 314. The outer-diameter biased coating further advantageously provides for a thin coating thickness, and a relatively smaller force is required to expand the sheath body 130 compared to a force required to expand a sheath having a coating without any bias. The outer-diameter biased coating also advantageously allows the sheath frame to expand and contract as desired, i.e., the outer-diameter biased coating does not immobilize the frame at a fixed diameter because the thin coating thickness is such that the coating does not encapsulate the portions of the frame where frame elements intersect. For example, for a braided frame having braided elements in an over-under braid pattern and an outer-diameter biased coating, the outer diameter biased coating advantageously is thin enough that it does not encapsulate an overlap of braided elements, i.e., the outer-diameter coating does not extend to the braided elements located under other braided elements in the over-under braided pattern.

In some implementations, the expandable sheath frame may have an expansion mechanism that aids the frame in expanding and/or contracting. For example, strands of a braided sheath frame may be configured with a bias to expand and/or contract from a resting position. According to some implementations, the expansion mechanism permits strands to slide relative to each other when the frame expands and contracts.

The expandable sheath body 130 and sheath tip 150 may be formed in a variety of ways, including using the configurations and methods of manufacture described in U.S. Patent Publication No. 2019/0247627A1 and/or U.S. Patent Publication No. 2018/0256859A1, which have been incorporated by reference herein. For example, the expandable sheath body 130 (and sheath tip 150) can be manufactured using thermal bonding or an outer-diameter biased dipping, which can provide the sheath body 130 with a smooth outer surface while retaining its desired spring-like expandable nature. Specific details of the possible configurations for sheath body 130 and methods of manufacturing them are included in the referenced published applications, and are thus not repeated in full herein.

By employing a frame and coating assembly as described above and in the referenced applications, the expandable sheath body 130 can expand and collapse while being resistant to kinking. This enables the sheath body 130 to expand to permit insertion or recovery of the medical device, and then return to its original shape after deformation. In addition, configuring the expandable sheath for compatibility with a dilator assembly and a stylet assembly aids in dilator insertion and removal, and improves hemostasis performance. Advantageously, the combination of a dilator assembly, an expandable sheath, and a hemostasis stylet provide a synergistic system which can be used relatively early in a procedure, e.g., in a catheterization lab rather than later in procedure, e.g., in surgery, when displacement of the pump could have more severe consequences for a patient. Because the system can be used relatively early in a procedure, potential pump migration can be addressed earlier, and vascular injury can be reduced.

Such an expandable sheath body 130 can also eliminate the need for the conventional set up of having multiple sheaths, such as a peel away introducer sheath and a repositioning sheath for the introduction of a medical device (e.g., an intracardiac heart pump) into the vessel opening (e.g., arteriotomy). In that regard, once the expandable sheath body 130 is positioned, it maintains access to a vessel even after the medical device is removed, should such access be required for other medical procedures. This increases procedural efficiency of any medical procedure and simplifies the process of inserting a component into the patient, as there is no need to peel away the introducer sheath for the insertion of a repositioning sheath each time access to the vessel opening is required. In addition, since the expandable introducer sheath body 130 need not be removed and replaced by a secondary repositioning sheath, the risk of premature tearing/peeling is essentially eliminated and the risk of shifting the introduced device inadvertently (e.g., by overuse of force) is reduced or eliminated. Furthermore, more accurate repositioning of the medical device can be achieved with the expandable introducer sheath as the expandable introducer sheath is fixed in position once inserted, whereas the insertion of a separate repositioning sheath involves multiple steps that increase the chances that the medical device will unintentionally be moved. Notwithstanding the foregoing, the expandable sheaths described herein may still be used in conjunction with a repositioning sheath.

FIG. 2 shows a dilator assembly 200 in accordance with aspects of the technology. The dilator assembly 200 has a dilator hub 230 at its proximal end, a dilator body 210, an interlock 240, and a dilator tip 220 at its distal end. As can be seen, dilator tip 220 tapers as it approaches its distal end, to facilitate insertion into the patient's vasculature. The dilator hub 230 is configured to engage the hub 110 of sheath assembly 100 as described further below.

Figure 3B:
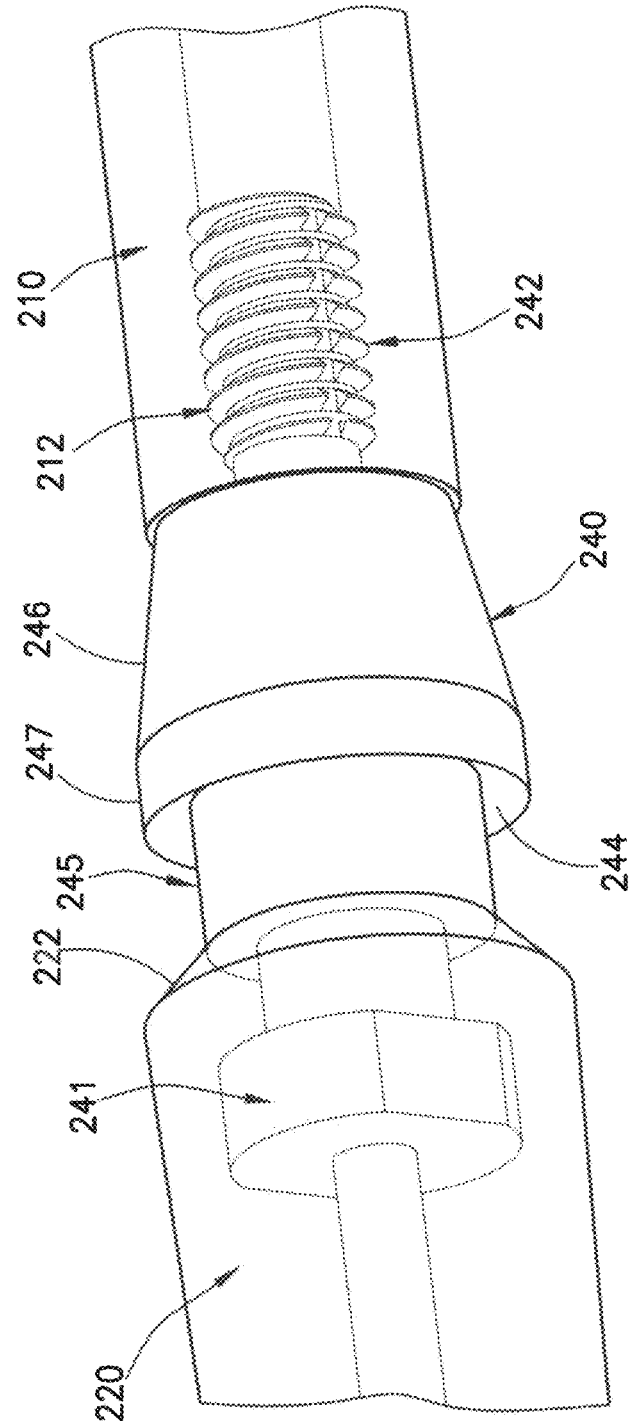

FIGS. 3A and 3B depict a cross-sectional and phantom view of a portion of a dilator assembly 200 in accordance with aspects of the technology. In that regard, FIG. 3A is a cross-sectional side view showing how the interlock 240 attaches to the dilator tip 220 and the dilator body 210, and FIG. 3B is a close-up isometric phantom view of the same assembly. As illustrated in FIGS. 3A and 3B, the distal end of interlock 240 is connected to the dilator tip 220 via flange 241. Flange 241 extends into the proximal end of dilator tip 220. In some implementations, the dilator tip 220 may be molded directly onto flange 241. The proximal end of interlock 240 is connected to dilator body 210 via a threaded connection. In that regard, the proximal end of interlock has a threaded male connector 242 which is received by a corresponding threaded female connector 212 on the distal end of the dilator body 210. Threaded male connector 242 and threaded female connector 212 may have any suitable diameter, pitch, specification, etc. For example, threaded male connector 242 and threaded female connector 212 may use a standard metric thread such as M1, M2, etc. Moving proximal to distal, the outer profile of interlock 240 is defined by a tapered waist 246 which begins at or near the outer diameter of dilator body 210 and increases in diameter until it reaches a cylindrical section 247 of constant diameter. Continuing in the distal direction, the cylindrical section 247 is followed by a recess 245 with a smaller outer diameter, and the transition between cylindrical section 247 and recess 245 forms a catch surface 244. Catch surface 244 and recess 245 are configured to engage with step 316 of sheath tip 150, as described further below. The length of tapered waist 246, cylindrical section 247, and recess 245 may be any suitable length. In some implementations, cylindrical section 247 may be between 0.5 mm and 20 mm in length. The proximal end of the dilator tip 220 has a transitional edge 222. Transitional edge 222 may be any suitable profile and angle. For example, transitional edge 222 may be a chamfer or a combination of two or more flat edges of different angles, may be curved in a concave or convex direction, or may be composed of one or more straight, convex, and/or concave sections.

Dilator tip 220, interlock 240, and dilator body 210 may be made of any suitable material. In some implementations, dilator tip 220 may be formed of a flexible material such as polyether block amide ("PEBA") with a durometer hardness of 40D. In some implementations, dilator tip 220 may be formed of other flexible materials such as PEBA with other hardness ratings, silicone, thermoplastic polyurethane ("TPU"), or thermoplastic elastomer ("TPE"). In some implementations, dilator tip 220 may further include hydrophilic lubricious coating such as polyvinylpyrrolidone ("PVP") or hyaluronic acid ("HA"), or a hydrophobic coating such as silicone or polytetrafluoroethylene ("PTFE"). In some implementations, dilator tip 220 may have no coating.

In some implementations, dilator body 210 may be formed of a semi-rigid material such as PEBA with a durometer hardness of 70D. In some implementations, dilator body 210 may be other semi-rigid materials such as PEBA with other hardness ratings, polyethylene, polypropylene, or polyurethane. In some implementations, heat may be applied to the threaded female connector 212 of dilator body 210 to increase its tensile strength and torque resistance.

In some implementations, interlock 240 may be formed of a rigid material such as 304 stainless steel. In some implementations, interlock 240 may be formed of other rigid metals such as 316 stainless steel, or rigid polymers such as polyether ether ketone ("PEEK"), acrylonitrile butadiene styrene ("ABS"), or polycarbonate. In some implementations, interlock 240 may be fully or partially coated, such as with a polymer. In some implementations, interlock 240 may have a coating that is between 0.025 and 0.2 mm. In some implementations, interlock 240 may have a coating with a durometer hardness of between 40A and 70D. In some implementations, interlock 240 may have a coating with a coefficient of friction that is greater than that of stainless steel and/or the material chosen for the dilator tip 220 or dilator body 210. In some implementations, interlock 240 may have no coating.

Figure 4:
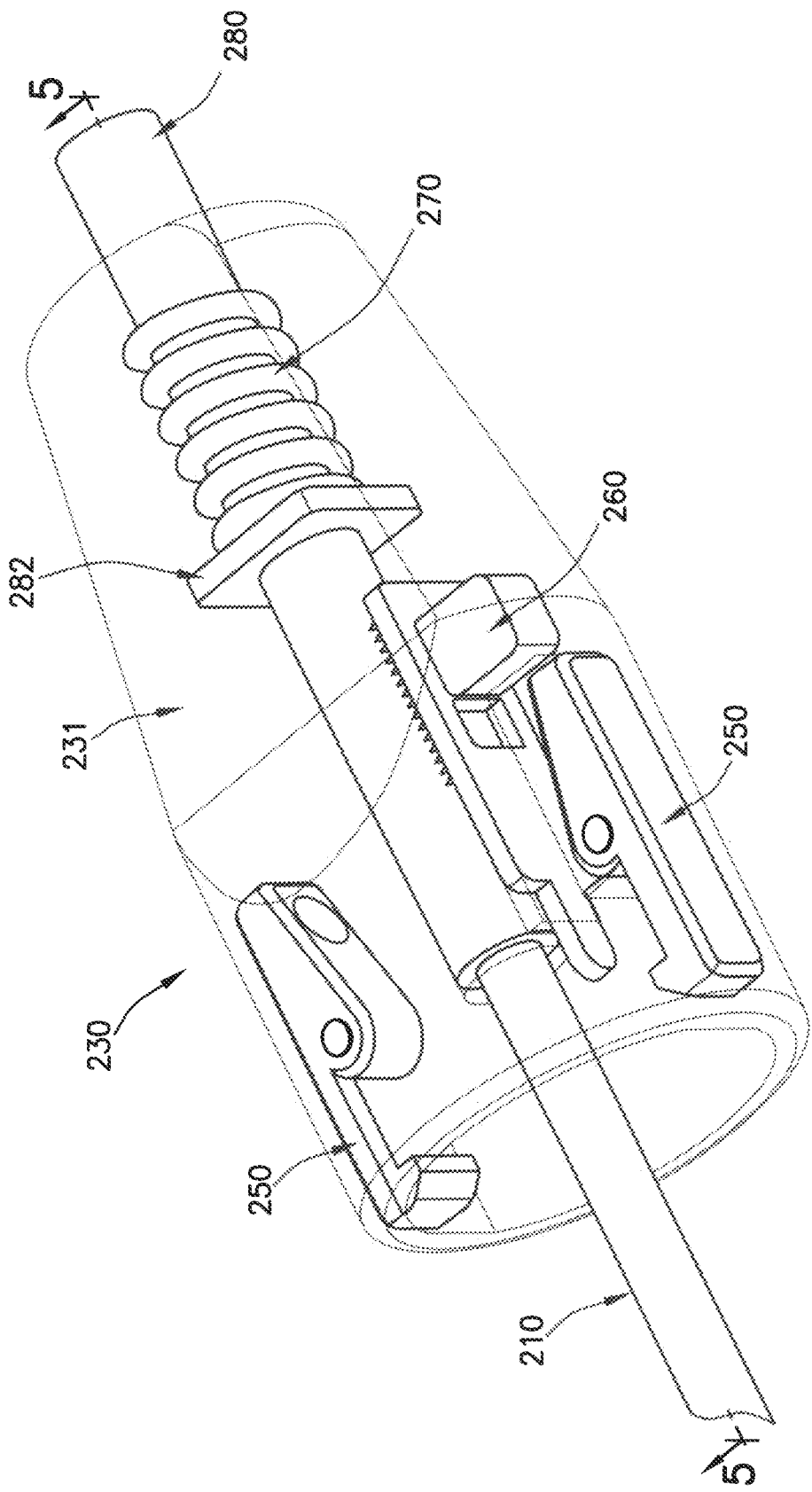
FIG. 4 is an isometric phantom view of the dilator hub of the dilator assembly of FIG. 2.

FIG. 4 shows an isometric view of a dilator hub 230 in accordance with aspects of the technology in which the outer housing 231 (comprised of two halves) is shown in phantom. As can be seen, dilator hub 230 has toothed latches 250 that secure it to the hub 110 of the introducer sheath assembly 100. The proximal end of dilator body 210 is coupled to a dilator insert mold 280. Dilator insert mold 280 has a flange 282 configured to engage with a spring 270 that is mounted within the proximal end of dilator hub 230. The spring 270 is configured to allow the dilator insert mold 280 to move in the proximal direction during attachment of dilator hub 230 with the hub 110 of sheath assembly 100. In that regard, the spring rate of spring 270 may be selected based on the modulus of elasticity of sheath body 130, in order to optimize the amount of tension applied to sheath body 130 as dilator hub 230 and hub 110 are pressed together into attachment, and sheath tip 150 is thus pulled in the distal direction. Likewise, the spring 270 may be preloaded to a certain tension or compression in order to optimize the amount of tension applied to sheath body 130 as dilator hub 230 and hub 110 are pressed together into attachment. In that regard, in some implementations, the spring rate of spring 270 may be between 0.1 N/mm and 3 N/mm, and it may have a travel between 1 mm and 20 mm. In some implementations, the force (including any preload) provided by the spring during attachment of dilator hub 230 to hub 110 may be between 5 N and 30 N.

As shown in FIG. 4, dilator hub 230 also has a lock 260 which is configured to engage with dilator insert mold 280. When brought into engagement with dilator insert mold 280, lock 260 will prevent dilator insert mold 280 from moving in the proximal or distal direction. By preventing movement in the proximal direction, lock 260 prevents the spring 270 from compressing as the dilator and sheath are inserted into a patient. Advantageously, by matching the spring rate and preloading of spring 270 with the modulus of elasticity of the sheath body 130, the sheath body 130 will be properly extended and tensioned when the dilator hub 230 is brought into attachment with hub 110, and thus lock 260 (once engaged) will maintain the sheath body 130 at this desired point of extension and tension. Lock 260 is configured to "close" or lock automatically upon attachment of dilator hub 230 and sheath body 130. However, in some implementations, lock 260 may instead be configured such that it must be actuated manually, such as by a button or switch. In addition, as the tension of the sheath body 130 will naturally resist further movement of the dilator body 210 in the distal direction, in some implementations, lock 260 may be configured to only prevent movement in the proximal direction.

Figure 5:
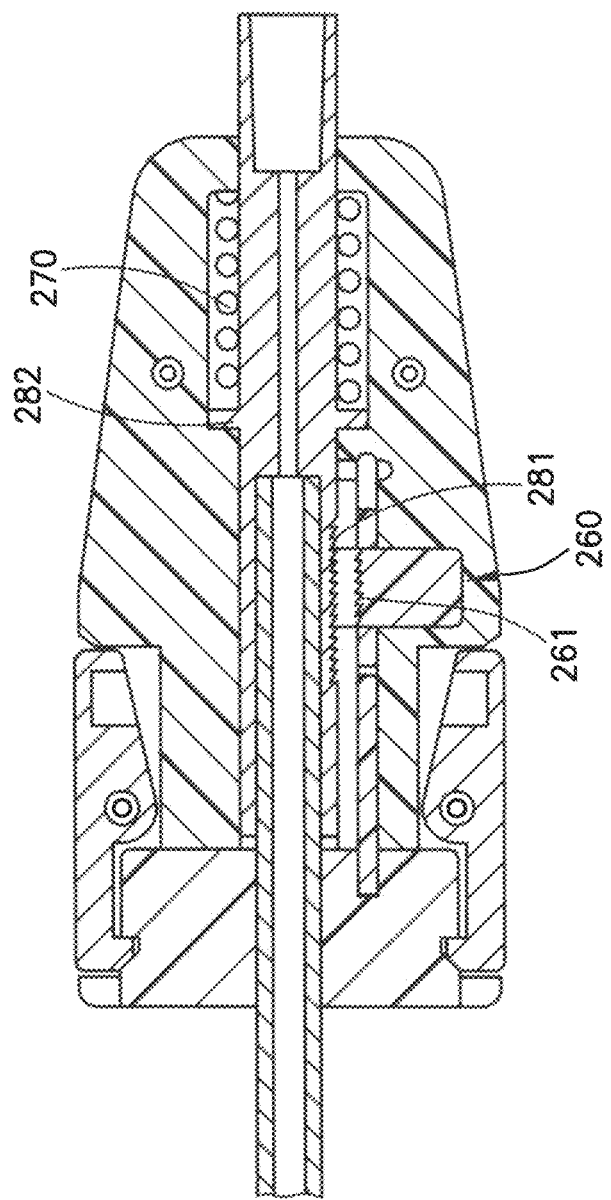
FIG. 5 is a cross-sectional side view of the dilator hub of the dilator assembly of FIG. 4.

FIG. 5 is a cross-sectional view of the dilator hub 230 of FIG. 4, divided along plane A-A of FIG. 4. As can be seen, lock 260 has teeth 261, and dilator insert mold 280 has teeth 281. FIG. 5 shows lock 260 in an "open" position such that dilator insert mold 280 can move within dilator hub 230. While FIG. 5 shows a toothed locking mechanism, lock 260 may be utilize any suitable mechanism for preventing movement of dilator insert mold 280.

Figure 6:
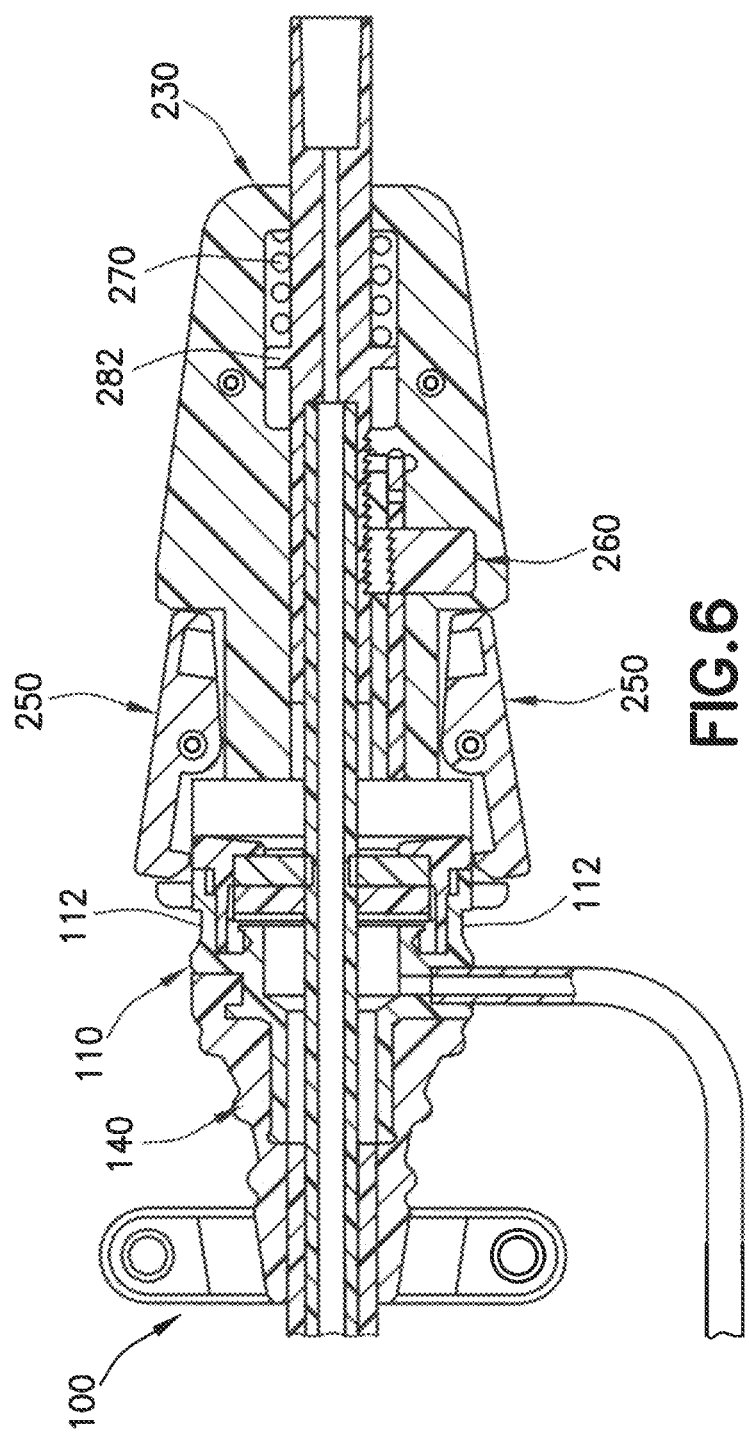
FIG. 6 is a cross-sectional side view of the dilator hub of the dilator assembly of FIG. 4 being attached to the sheath assembly of FIG. 1.

FIG. 6 is a cross-sectional side view of the dilator hub 230 of FIG. 4 in the process of being attached to a hub 110 of sheath assembly 100, in accordance with aspects of the technology. As can be seen from FIG. 6, the toothed latches 250 of dilator hub 230 are both in an open position, and have not yet engaged with detents 112 in hub 110. Likewise, lock 260 is still shown in an "open" position such that dilator insert mold 280 can move within dilator hub 230. In that regard, dilator insert mold 280 is shown having begun to compress spring 270 in the proximal direction, as will occur when the dilator hub 230 and hub 110 are pressed together into attachment, and sheath tip 150 is thus pulled in the distal direction.

Figure 7:
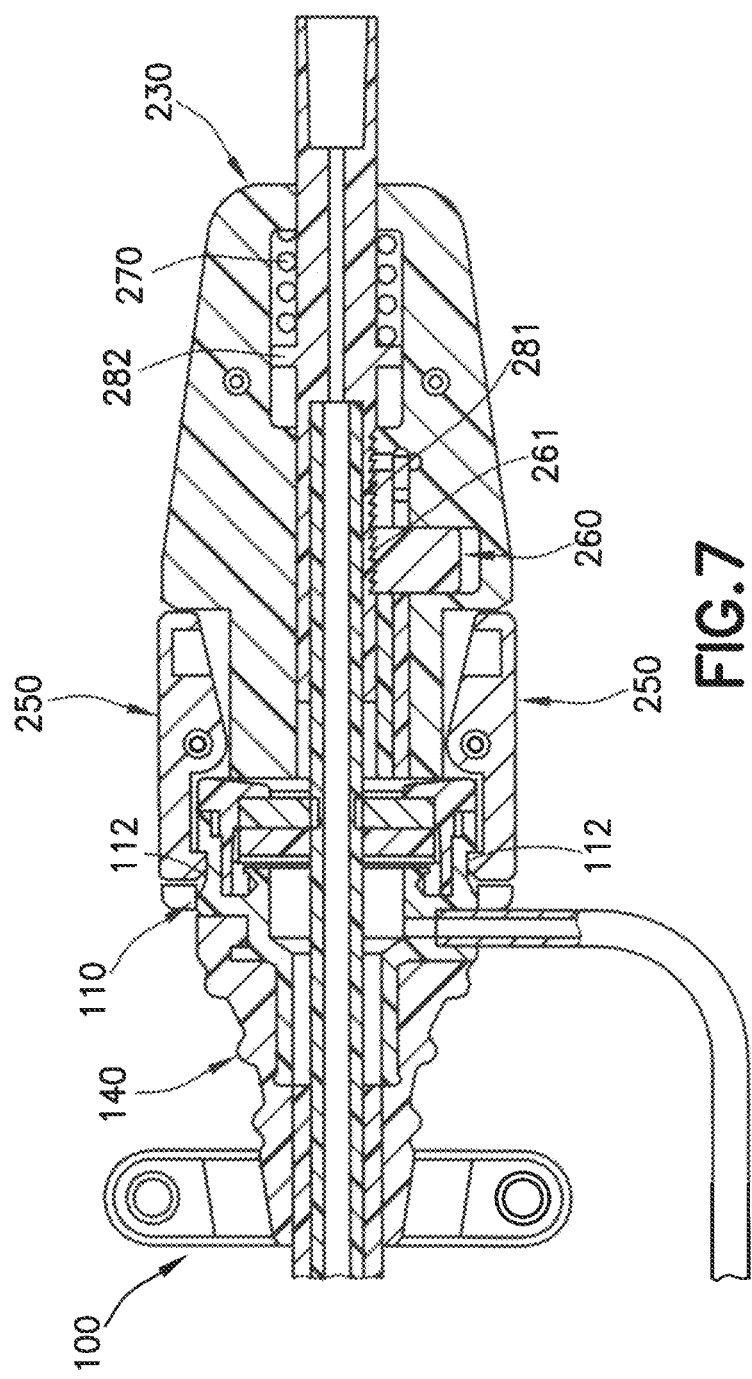
FIG. 7 is a cross-sectional side view of the dilator hub of the dilator assembly of FIG. 4 locked onto the sheath assembly of FIG. 1.

FIG. 7 illustrates the dilator hub 230 of FIG. 4 locked into the hub 110 of sheath assembly 100, in accordance with aspects of the technology. As can be seen from FIG. 7, the toothed latches 250 have engaged with detents 112 in hub 110, thus providing a clamping force that prevents the dilator hub 230 from being able to be pulled away from hub 110. In addition, lock 260 is shown in a "closed" position, in which it has moved radially inward within dilator hub 230 such that its teeth 261 engage teeth 281 of the dilator insert mold 280. The engagement of teeth 261 and 281 provides resistance against dilator insert mold 280 being pushed further into dilator hub 230 in the proximal direction. As discussed above, by tuning of the spring rate and preloading of spring 270 relative to the modulus of elasticity of sheath body 130, the assembly can be configured such that sheath body 130 is brought to a desired tension at the point that dilator hub 230 locks into hub 110. Lock 260 can then be applied (e.g., manually or automatically as a result of dilator hub 230 locking into hub 110), thus maintaining sheath body 130 at that desired tension and preventing the dilator insert mold 280 from moving in the proximal direction as the dilator and sheath are inserted into a patient.

Figure 8:
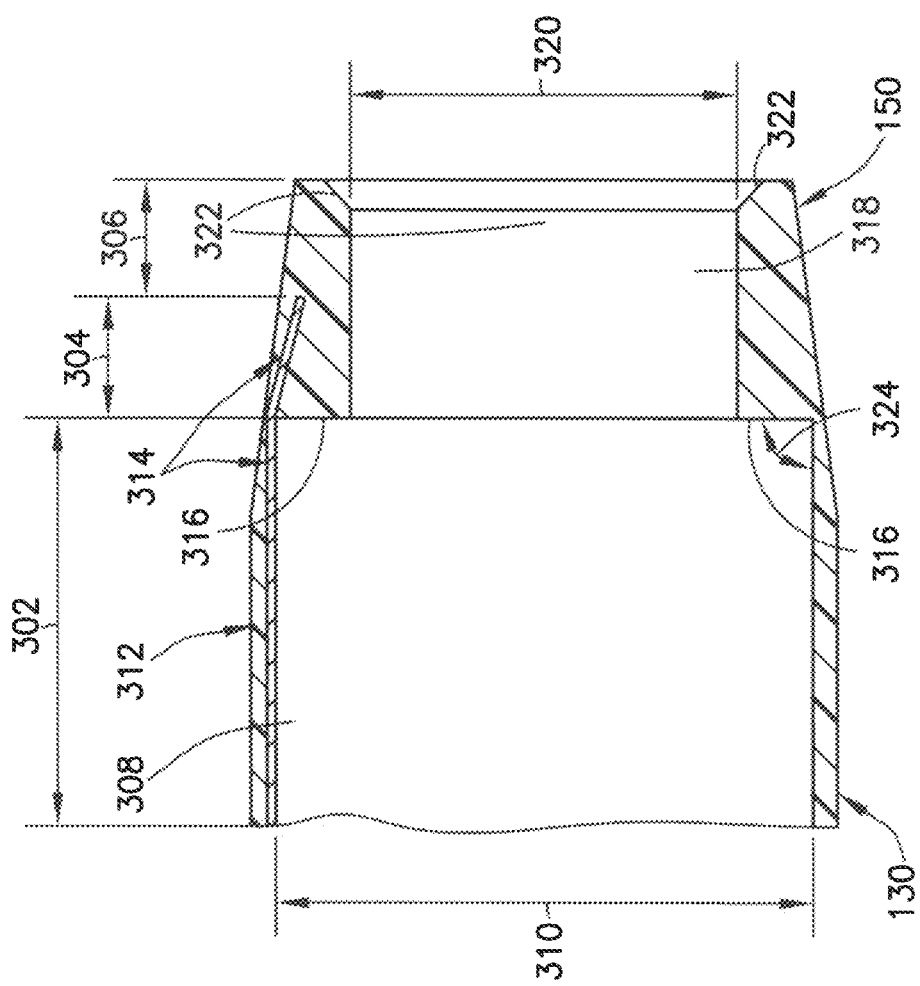
FIG. 8 is a cross-sectional side view of a distal end of the sheath assembly of FIG. 1 according to aspects of the disclosure.

FIG. 8 is a cross-sectional side view of the distal end of sheath assembly 100, showing an example of how the distal end of sheath body 130 and sheath tip 150 may be configured. The structure of FIG. 8 will be discussed with respect to three portions, 302, 304, and 306. In the first portion 302, the sheath body 130 has a cavity 308 with an inner diameter 310. The outer surface of first portion 302 is a polymer material 312. The inner surface of first portion 302 is a braided material 314. Braided material 314 may be any suitable material, as describe above and in the referenced publications. In some implementations, braided material 314 may be composed of strands of a flexible metal such as Nitinol. As noted above, in some implementations, an additional lubricious coating (not shown) may be applied to the inner and/or outer surfaces of sheath body 130, i.e., covering polymer material 312 and/or braided material 314. In some implementations, the polymer material 312 is thermoplastic polyurethane ("TPU"), and it is bonded to the braided material 314 using a thermoforming process. On the inner surface of sheath body 130, there is a step 316 between the first portion 302 and the second portion 304. Step 316 forms an angle 324 with the inner surface of the first portion 302, and creates a cavity 318 with a second inner diameter 320 that is smaller than the inner diameter 310 of cavity 308. In FIG. 8, angle 324 is shown as a right angle, i.e., 90°. However, angle 324 may be any angle that allows for step 316 to suitably engage with catch surface 244 of interlock 240 as described further below. Thus, in some implementations, angle 324 may an obtuse angle, or an acute angle (e.g., as depicted and described with respect to FIG. 9, below). Step 316 may be any suitable height. In some implementations, step 316 may be between 0.1 mm and 1 mm.

In the second portion 304, the braided material 314 of the sheath tip 150 is sandwiched between polymer material 312. As a result, polymer material 312 forms both the inner and outer surfaces of the second portion 304. In addition, as can be seen, where the sheath body 130 transitions to sheath tip 150, the outer surface begins tapering down in diameter. This tapering begins near the distal end of the first portion 302, and the taper continues through the second portion 304 and the third portion 306. Similarly, the braided material 314 also has both a cylindrical section and a tapered section. As shown in FIG. 8, the tapered section of braided material 314 begins at the division between the first portion 302 and the second portion 304. However, in other implementations, the tapered section of braided material 314 may begin more proximally (i.e., somewhere within the first portion 302) or more distally (i.e., somewhere within the second portion 304 or third portion 306) than is shown in FIG. 8.

In the third portion 306, sheath tip 150 is composed entirely of polymer material 312. As shown in FIG. 8, the inner surface of the third portion 306 has transitional edge 322 at its distal end. Transitional edge 322 is shown in FIG. 8 as a chamfer. However, transitional edge 322 may be a fillet or any other suitable contour. Further, transitional edge 322 is optional. Thus, in some implementations, the third portion 306 may have a constant inner diameter equal to inner diameter 320, and transitional edge 322 may be replaced with a squared corner.

In some implementations, the surfaces of cavity 318 and/or transitional edge 322 may be textured or otherwise configured to reduce friction and stiction between those surfaces of sheath tip 150 and other devices that pass through it, e.g., the dilator tip 220, interlock 240, interventional devices introduced through sheath assembly 100 such as intracardiac heart pumps, etc. Texturing may be applied to the surfaces of cavity 318 and/or transitional edge 322 in any suitable method. For, example, texturing may be applied to sheath tip 150 by forming it using a mandrel which itself has been textured through machining, sand-blasting, shot peening, chemical etching, laser surface texturing, etc. In that regard, in some examples, the surfaces of cavity 318 and/or transitional edge 322 may be cross-hatched, knurled, or dimpled. In some examples, the surfaces of cavity 318 and/or transitional edge 322 may have a pattern composed of dashed or continuous lines, which may extend in any direction, e.g., longitudinally, circumferentially, or any angle therebetween. In some examples, the surfaces of cavity 318 and/or transitional edge 322 may have a pattern of lines that are curvilinear, sinusoidal, saw-toothed, or any combination thereof, and which may extend in any direction, e.g., longitudinally, circumferentially, or any angle therebetween. In some examples, the surfaces of cavity 318 and/or transitional edge 322 may have one or more raised or recessed grooves, which may extend in any direction, e.g., longitudinally, circumferentially, or any angle therebetween. Likewise, in some examples, the surfaces of cavity 318 and/or transitional edge 322 may be coated or comprised of materials that reduce friction or stiction. For example, the surfaces of cavity 318 and/or transitional edge 322 may have a lubricious coating, or polymer material 312 may be a material with a suitably low coefficient of friction, e.g., PTFE. The surfaces of cavity 318 and/or transitional edge 322 may incorporate any combination of the different options described above, including a combination of textured features as well as lubricious coatings and/or low-friction materials.

FIG. 9 is a cross-sectional side view of the distal end of sheath assembly 100, showing an additional example of how the distal end of sheath body 130 and sheath tip 150 may be configured. All features of the implementation of FIG. 9 are identical to those shown in FIG. 8, with the exception of the transition between inner diameter 310 and 320. In that regard, in FIG. 9, the angle 324 between the inner surface of the first portion 302 and step 316 is acute, i.e., less than 90°. Again, angle 324 may be any angle that allows for step 316 to suitably engage with catch surface 244 of interlock 240 as described further below. For example, in some implementations, angle 324 may be an acute angle, e.g., between 30° and 89°.

FIG. 10A is a cross-sectional view of an implementation of the dilator body 210, interlock 240, and dilator tip 220 in accordance with aspects of the technology. FIG. 10B illustrates a close-up cross-sectional view of the components of FIG. 10A in engagement with the sheath tip 150 of FIG. 8. FIGS. 10A and 10B show a generalized embodiment in which the flange 241 and threaded male connector 242 of interlock 240, and the threaded female connector 212 of dilator body 210 have been omitted. One of ordinary skill in the art will understand that the dilator body 210, interlock 240, and dilator tip 220 may be coupled to one another in a variety of ways including, but not limited to, those shown in FIGS. 3A and 3B above. In that regard, dilator body 210, interlock 240, and dilator tip 220 may be bonded, glued, or welded to one another. Likewise, dilator body 210, interlock 240, and dilator tip 220 may be coupled using additional fasteners. In some implementations, one or more of dilator body 210, interlock 240, and dilator tip 220 may be formed as unitary structures, or joined as a result of overmolding. To arrive at the assembly of FIG. 10B, the dilator tip 220 is pushed through the distal end of sheath tip 150. As discussed above, sheath tip 150 may be configured to expand as the tapered dilator tip 220 is passed through it. Thus, sheath tip 150 may be configured so that it must expand to pass over transitional edge 222 of dilator tip 220, and then naturally contracts again as it reaches the narrower recess 245 of interlock 240. As dilator tip 220 continues to be pushed in the distal direction, step 316 of sheath tip 150 will come into contact with catch surface 244 of interlock 240, as shown in FIG. 10B. Catch surface 244 meets up with the surface of recess 245 at an angle 248. Like angle 324, angle 248 can be any angle that allows for step 316 to suitably engage with catch surface 244 of interlock 240 as described. Thus, in some implementations, angle 248 may be a right angle. In some implementations, angle 248 may be an acute angle, e.g., between 30° and 89°. In some implementations, angle 248 may be an obtuse angle. In some implementations, angle 248 may be different than angle 324, such as in FIG. 10B. In some implementations, angle 248 may be identical or substantially identical to angle 324, such as in FIG. 11, which illustrates a close-up cross-sectional view of the components of FIG. 10A in engagement with the sheath tip 150 of FIG. 9. All features of the implementation of FIG. 11 are identical to those shown in FIG. 10B, with the exception that angle 248 is identical or substantially identical to angle 324 in the implementation of FIG. 11.

Figure 11:
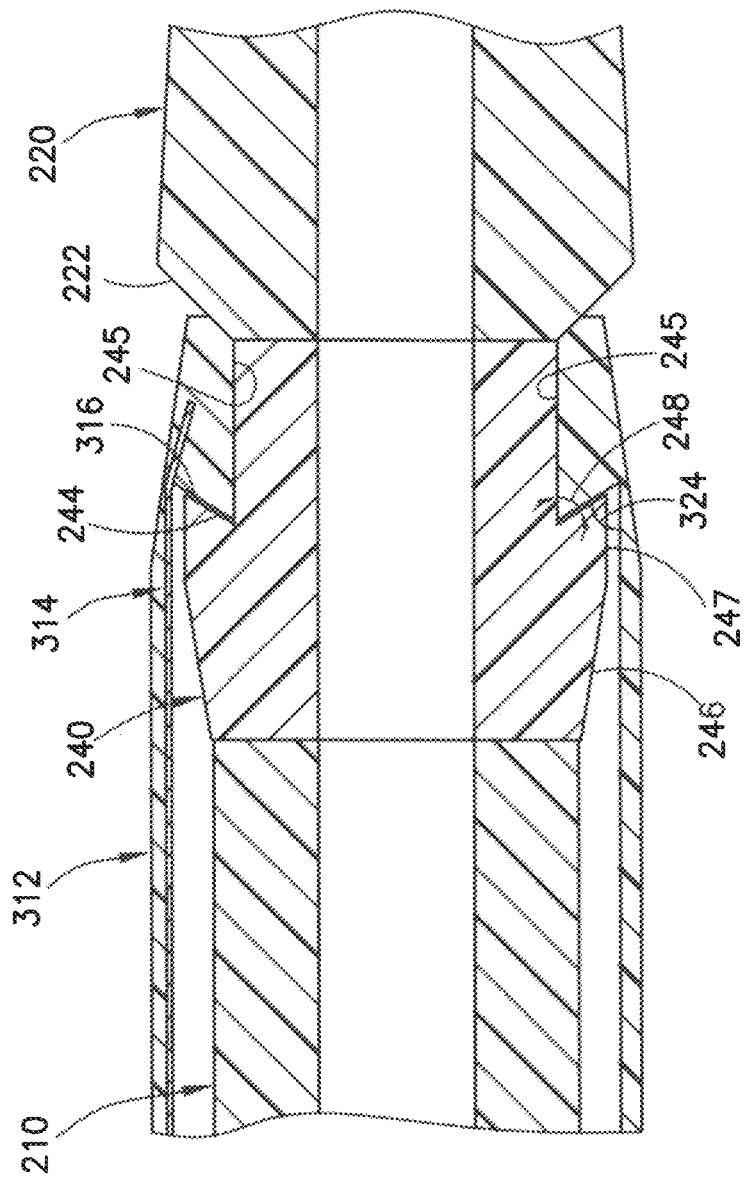
FIG. 11 is a close-up cross-sectional view of the components of FIG. 10A in engagement with the sheath tip of FIG. 9.

Once the catch surface 244 of interlock 240 engages step 316 of sheath tip 150 as shown in FIG. 10B and FIG. 11, pushing the dilator tip 220 further in the distal direction will pull the sheath tip 150 and thus begin to tension the sheath body 130, causing it to elongate and narrow. Drawing down the sheath body 130 in this way advantageously reduces its insertion profile, which helps to minimize patient complications (e.g., bleeding, vascular injury, high insertion forces). At this point, the dilator assembly 200 may be used to insert the sheath tip 150 and sheath body 130 into the patient's vasculature.

Once the sheath body 130 has been positioned as desired within the patient's vasculature, the dilator hub 230 may be unlocked from the hub 110 of sheath assembly 100 by pressing toothed latches 250 and pulling the dilator hub 230 in the proximal direction. By continuing to retract the dilator assembly 200 in the proximal direction while sheath tip 150 remains stationary, catch surface 244 will be pulled away from step 316, and the transitional edge 222 of dilator tip 220 will move past sheath tip 150, allowing dilator assembly 200 to be fully retracted from the patient. The sheath assembly 100 may then be used to introduce the intracardiac blood pump and/or other components into the patient's vasculature as discussed further above. Notably, as sheath body 130 will no longer be in tension after dilator assembly 200 has been withdrawn, sheath body 130 will be free to relax into a shorter and wider configuration that aids in insertion of such components.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An apparatus, comprising:
   a sheath comprising:
      a frame having a proximal opening, a distal opening, an inner surface, and an outer surface wherein the proximal opening is configured to receive a dilator; and
      a material covering the outer surface of the frame and a portion of the inner surface of the frame, and forming a step feature within the distal opening, the step feature having a first surface that abuts the inner surface of the frame and that is oriented at a first angle relative to the inner surface of the frame; and
   a dilator comprising:
      a body;
      a tapered tip comprising at least a first tapered section and a second tapered section being proximal of the first tapered section, wherein the first tapered section decreases in diameter in a distal direction and the second tapered section decreases in diameter in a proximal direction; and
      an interlock between the body and the tapered tip having a first cylindrical section with a first outer diameter, a second cylindrical section with a second outer diameter that is less than the first outer diameter, and a catch surface that abuts the first cylindrical section and that is oriented at a second angle relative to the first cylindrical section, wherein the interlock is connected to the body by a threaded connection and is connected to the tip by flange; and wherein the catch surface is configured to engage the first surface to resist the body of the dilator from passing out of the frame through the distal opening.

2. The apparatus of claim 1, wherein the sheath is expandable, the sheath further comprising:
a sheath hub configured to secure the expandable sheath proximate to the distal opening of the expandable frame; and
a dilator hub comprising:
a dilator insert mold configured to secure the body of the dilator;
a spring configured to engage the dilator insert mold, and resist movement of the dilator insert mold within the dilator hub; and
one or more latches configured to lock the dilator hub to the sheath hub.

3. The apparatus of claim 2, wherein the frame is a cylindrical or substantially cylindrical expandable frame.

4. The apparatus of claim 3, wherein the material covering the outer surface of the expandable frame and a portion of the inner surface of the expandable frame further comprises a tapered inner edge at a distal end of the expandable sheath, the tapered inner edge being configured to engage the second tapered section of the tapered tip when the catch surface of the interlock is in engagement with the first surface of the sheath.

5. The apparatus of claim 3, wherein the material is a polymer.

6. The apparatus of claim 5, wherein the material is thermoplastic polyurethane.

7. The apparatus of claim 6, wherein the expandable frame is a braided material.

8. The apparatus of claim 7, wherein the braided material comprises strands of nitinol.

9. The apparatus of claim 6, wherein the expandable sheath further comprises a coating applied to the expandable frame and the material.

10. The apparatus of claim 9, wherein the coating is a lubricious coating.

11. The apparatus of claim 1, wherein the first angle is ninety degrees.

12. The apparatus of claim 1, wherein the first angle is less than ninety degrees.

13. The apparatus of claim 1, wherein the second angle is ninety degrees.

14. The apparatus of claim 1, wherein the second angle is less than ninety degrees.

15. The apparatus of claim 1, wherein the step feature has a radial height of between 0.1 mm and 5 mm.

16. The apparatus of claim 1, wherein the interlock is formed of stainless steel.

17. The apparatus of claim 16, wherein the interlock is coated with a polymer.

18. The apparatus of claim 1, wherein the interlock is formed of a polymer.

19. The apparatus of claim 18, wherein the tapered tip is formed of polyether block amide.

20. The apparatus of claim 1, wherein the tapered tip is formed of a polymer.

21. The apparatus of claim 1, wherein the second tapered section comprises a transitional edge, and a distal end of the sheath comprises a complementary inner edge.

22. The apparatus of claim 21, wherein the transitional edge is filleted, and a distal end of the sheath comprises a complementary rounded inner edge.

23. The apparatus of claim 21, wherein the transitional edge is rounded, and a distal end of the sheath comprises a complementary filleted inner edge.

24. The apparatus of claim 21, wherein the transitional edge comprises a chamfer, and a distal end of the sheath comprises a complementary chamfered inner edge.

25. The apparatus of claim 1, wherein at least a portion of an inner surface at a distal end of the sheath is textured with a cross-hatched pattern.

26. The apparatus of claim 1, wherein at least a portion of an inner surface at a distal end of the sheath is textured with a knurled pattern.

27. The apparatus of claim 1, wherein at least a portion of an inner surface at a distal end of the sheath is textured with a dimpled pattern.

28. The apparatus of claim 1, wherein at least a portion of an inner surface at a distal end of the sheath is textured with a pattern of dashed or continuous parallel lines.

29. The apparatus of claim 1, wherein at least a portion of an inner surface at a distal end of the sheath is textured with a pattern of dashed or continuous curvilinear lines.

30. The apparatus of claim 1, wherein at least a portion of an inner surface at a distal end of the sheath is textured with a pattern of dashed or continuous saw-toothed lines.

31. The apparatus of claim 1, wherein at least a portion of an inner surface at a distal end of the sheath comprises one or more recessed grooves.

32. The apparatus of claim 1, wherein at least a portion of an inner surface at a distal end of the sheath comprises one or more raised grooves.

33. The apparatus of claim 1, wherein at least a portion of an inner surface at a distal end of the sheath has a lubricious coating.

* * * * *